(12) United States Patent
Kijima

(10) Patent No.: US 6,203,821 B1
(45) Date of Patent: Mar. 20, 2001

(54) ACTIVE WATER

(76) Inventor: Ryodo Kijima, 8-14-302, Wise-Trade, Higashisuna 4-chome, Koto-ku Tokyo (JP)

( * ) Notice: Subject to any disclaimer, the term of this patent is extended or adjusted under 35 U.S.C. 154(b) by 0 days.

(21) Appl. No.: 08/863,211

(22) Filed: May 27, 1997

(30) Foreign Application Priority Data

| Jun. 1, 1996 | (JP) | 8-161174 |
| May 2, 1997 | (JP) | 9-130373 |

(51) Int. Cl.$^7$ .......... A61K 33/26; A61K 31/28; A01N 55/02; A01N 59/16
(52) U.S. Cl. .......... 424/647; 424/646; 424/648; 424/650; 514/492; 426/74; 422/22
(58) Field of Search .......... 424/647, 648, 424/650, 646; 514/492; 426/74; 422/22

(56) References Cited

U.S. PATENT DOCUMENTS 4,797,156 * 1/1989 Yamashita .......... 428/472.2
5,008,097 * 4/1991 Yamashita .......... 423/493

FOREIGN PATENT DOCUMENTS

| 62-74268 | * 4/1987 | (JP) . |
| 63593 | 10/1991 | (JP) . |
| 3224690 | * 10/1991 | (JP) . |
| 27171 | 5/1992 | (JP) . |
| 61822 | 3/1995 | (JP) . |

OTHER PUBLICATIONS

Chemical Abstracts 107: 38390t (1987).*
Chemical Abstracts 116: 45990c (1992).*

* cited by examiner

*Primary Examiner*—John Pak
(74) *Attorney, Agent, or Firm*—Fish & Richardson P.C.

(57) ABSTRACT

An active water is disclosed, comprising water having a substance containing a divalent and trivalent iron salt component and an organogermanium compound and/or a seawater concentrated solution contained therein, the active water of the invention possessing superior functions including pharmacological and physiological functions and being effective for the medicinal use.

5 Claims, No Drawings

ACTIVE WATER

FIELD OF THE INVENTION

The present invention relates to an active water and in particular, to an active water having superior functions including pharmacological and physiological functions, growth promotion functions for animals and plants, freshness retention functions for animals and plants, and corrosion prevention and rust prevention functions.

BACKGROUND OF THE INVENTION

In general, as processing processes for activating water to produce an active water, the electromagnetic wave processing for utilizing ultrasonic wave or the like, the chemical processing for acting ozone or the like, the water purifying processing of superpure water, and others have hitherto been known. By these processing processes, active waters having respective characteristics have been obtained.

In addition, in recent years, the investigations of the life chemistry have been promoted to attain the development of a novel active substance of divalent and trivalent iron salt, $Fe^{+2}{}_mFe^{+3}{}_nCl_{2m+3n}$, in which m and n each represents a variable. This active substance is an inorganic salt (e.g., hydrochlorides, sulfates, nitrates, etc.) or organic salt (e.g., formates, acetates, propionates, etc.) of iron having intermediate natures between divalent iron and trivalent ion. For example, this active substance can be obtained in a transition state in the case where ferric chloride is thrown into an aqueous solution of strong alkalis such as sodium hydroxide, calcium hydroxide, potassium hydroxide, and lithium hydroxide to cause the valence conversion and therefore, can presently be produced on an industrial scale (see Japanese Patent Publication Nos. 3-63593 and 4-27171).

It has been clarified that the foregoing active substance of divalent and trivalent iron salt has the following functions upon being brought into contact with water. That is, it is noted that if a very slight amount (concentration: $2\times10^{-12}$ ml=1/20,000,000,000,000) of this active substance is mixed in the usual water, an aqueous 1/20,000,000,000,000 wt % solution of the substance (hereinafter, this aqueous solution being referred to as "π water" for the sake of convenience) has the following characteristics.

(Structure change of water molecule)

Usually, since in the water molecule, the centers of gravity of hydrogen and oxygen do not overlap each other, the plus/minus polarity occurs. For this reason, since the water molecules are bonded to each other in a cage-like state due to the hydrogen bonding, hydrocarbons, methane, gases, and the like are dissolved into the cage. On the other hand, in the π water, the bonding structure between the water molecules is changed from the polar molecule to the non-polar molecule due to the electron spin, i.e., the centers of gravity of H (hydrogen) and O (oxygen) are made overlap each other, whereby the bipolarity becomes null. In another word, the water molecules themselves no longer have a plus or minus polarity and as a result, it may be considered that the structure of the water molecule changes from the cage-like state to the string-like state. For this reason, the hydrocarbons and the like are not dissolved thereinto not like the usual water.

(Deionization reaction)

Usually, metals or metallic salts are subjected to ionic dissociation in water, whereby substance changes mainly consisting of ionization reaction occur. On the other hand, since in the π water, there is neither plus polarity nor minus polarity, dedissociation of metallic ions occurs, thereby forming a nonionic reaction system.

(Change of expansion coefficient of gas)

In the case where the (water is present together with a gas (air) in the same system, the apparent expansion coefficient of the gas against the temperature changes depending on the temperature. That is, though in the case of distilled water, the air volume linearly expanded in proportion to the increase in the temperature, in the case of the π water, the air volume changed along the curve having an inflection point in the vicinity of 22° C.

(Change of potential difference)

Usually, in water, the potential difference elevates with an increase of metallic ions. On the other hand, since in the π water, metallic ions are subjected to deionization dissociation, the potential difference is lowered, leading to the removal of heavy metallic ions.

(Stabilizing effect of pH)

Usually, the pH is determined depending on the degrees (amounts) of acidic substances and alkaline substances contained in water. On the other hand, in the π water, acidic substances (e.g., sulfide ions, etc.) and alkaline substances (e.g., hydroxide ions, etc.) are controlled and subjected to deionization dissociation, whereby the pH is made neutral and stabilized.

(Interception of pathogenic fungi)

Various fungi including bacteria are unicellular microorganisms and have a minus charge. These various fungi inhabit in an ionic reaction system of the usual water. On the other hand, in the π water, the ionic reaction is inhibited, and the equilibrium condition of the various fungi is changed, thereby changing the system to a circumstance where the various fungi can no longer multiply.

As described above, the foregoing substances are experimentally proven to change the structure of the water molecule, thereby activating the water and are presently widely used as modification activators. Nowadays, the investigations and experiments have further been made especially as to the processes of pharmacological and physiological use of the above-described π water, resulting in obtaining noteworthy results.

In addition, as other processing processes for modifying and activating the water to produce an active water, an electromagnetic processing process for giving a magnetic field, an electric field, or the like to water is drawing attention. In general, if a considerably strong magnetic field of 1 terrace (=$10^4$) is applied to water, the energy which the water can obtain is about 10 s/mol based on the calculation of the magnetic field energy, the value being remarkably smaller than the values of the thermal motion energy of water and the hydrogen bonding energy of water. For these reasons, it was hard to consider that this magnetic field energy strongly acts the energy which the water possesses, thereby changing the nature of water. However, in 1977, the "Magnetization Processing of Water" was reported by B. E. Classen, USSR, and thereafter, it has been widely known that this processing is useful for giving various effects as an active water, so that the thus-processed active water is being put into practice in not only Europe and America but also Japan.

Although the mechanism how the magnetic field acts on the water has not yet been clarified in detail, the structure of water always changes, the time for which a constant structure is kept is about $10^{-12}$ second, and association and dissociation are repeated. At this point, it may be considered that the magnetic field influences such association and dissociation.

The present inventor paid attention to the above-described facts and made extensive investigations and experiments and as a result, developed a novel active substance of magnetic divalent and trivalent iron salt (see Japanese Patent Application Laid-Open No. 7-61822). This active substance of divalent and trivalent iron salt is an active substance capable of modifying and activating water, which simultaneously possesses both of the characteristics due to the electromagnetic processing and those due to the chemical processing. Though the active substance of divalent and trivalent iron salt is obtained by, for example, chemically processing a magnetite, its production process and the like will be described later in detail.

The above-described active substance of magnetic divalent and trivalent iron salt is brought into contact with water and acts so as to have the following characteristics. That is, if a very slight amount (concentration: $2 \times 10^{-12}$ ml=1/20,000,000,000,000) of this active substance is mixed in the usual water, an aqueous 1/20,000,000,000,000 wt % solution of the substance (hereinafter, this aqueous solution being referred to as "π water" for the sake of convenience) possesses the same characteristics as in the active water having been subjected to electromagnetic processing, in addition to the characteristics which the π water possesses as described above. In particular, since this active substance is dissolved in water and co-present therein, it acts on the water more strongly and effectively as compared with the active water having a magnetic field applied thereto externally. This active substance can be used as a modification activator of water like the substance of the π water as described above, and this magnetic π water has a possibility for the pharmacological and physiological use like the above-described π water.

As described above, each of the π water and the magnetic π water is an active water which can be widely used and has a possibility for the medicinal use. However, these π water and magnetic π water, as they stand, are not yet satisfactory for the medicinal use, and there is room for further improvements.

SUMMARY OF THE INVENTION

Under these circumstances, the present invention has been made. That is, an object of the present invention is to provide a novel active water which is not only so useful as to be widely used but also possesses both of the pharmacological function and the physiological function.

In order to solve the aforesaid problems, the present inventor made extensive and intensive investigations and as a result, has achieved the foregoing object, leading to the present invention.

DETAILED DESCRIPTION OF THE INVENTION

The active water as one of the invention according to the present invention comprises water having a substance containing a divalent and trivalent iron salt component and an organogermanium compound and/or a seawater concentrated solution contained therein.

Examples of the substance containing a divalent and trivalent iron salt component include compounds represented by the following formula (1):

$$Fe^{+2}{}_m Fe^{+3}{}_n Cl_{2m+3n} \tag{1}$$

wherein m and n each represents a variable.

As described above, the substance represented by the formula (1) is an inorganic salt (e.g., hydrochlorides, sulfates, nitrates, etc.) or organic salt (e.g., formates, acetates, propionates, etc.) of iron having intermediate natures between divalent iron and trivalent iron. For example, this substance can be obtained in a transition state in the case where ferric chloride is thrown into an aqueous solution of strong alkalis such as sodium hydroxide, calcium hydroxide, potassium hydroxide, and lithium hydroxide to cause the valence conversion. As a specific production process of this substance, one comprising the following steps is exemplified. That is, the substance is produced by a process comprising a step for dissolving ferric chloride in an aqueous strong alkali solution, a step for neutralizing the solution with hydrochloric acid, and a step for concentrating the neutralized solution to obtain crystals.

In the present invention, though the active substance ($Fe^{+2}{}_m Fe^{+3}{}_n Cl_{2m+3n}$) thus produced through these steps can be used alone, it can be supported on a carrier substance comprising, for example, an inorganic compound such as sodium chloride, sodium sulfate, ammonium chloride, diatomaceous earth, bentonite, silica, and aluminum, or an organic compound such as vitamins, hormones, proteins, and amino acids. Even in the latter case, the active substance can maintain its effects and efficiently work.

Examples of the organogermanium compound include those represented by the following formulae:

(2)
$(GeCH_2 \quad CH_2 \quad COOH)_2 O_3$

(3)
$CH_3$
$|$
$(GeCH \quad CH_2 \quad COOH)_2 O_3$

(4)
$CH_3$
$|$
$(GeCH_2 \quad CH \quad COOH)_2 O_3$

(5)
$CH_3 \quad CH_3$
$| \quad\quad |$
$(GeCH \quad CH \quad COOH)_2 O_3$

(6)
$CH_3$
$|$
$(GeC \quad CH_2 \quad COOH)_2 O_3$
$|$
$CH_3$

(7)
$C_6H_5$
$|$
$(GeCH \quad CH_2 \quad COOH)_2 O_3$

(8)
$C_6H_5 \quad CH_3$
$| \quad\quad |$
$(GeCH \quad CH \quad COOH)_2 O_3$

(9)
$(GeCH_2 \quad CH_2 \quad COOCH_3)_2 O_3$

(10)
$(GeCH_2 \quad CH_2 \quad CONH_2)_2 O_3$

(11)
$(GeCH_2 \quad CH_2 \quad COO^-Na^+)_2 O_3$

While any of these organogermanium compound can be used for the object of the present invention, it is to be construed that they are merely enumerated as one specific example and are not limited to the above-described specific examples. It has been proven from reports that the organogermanium compound has a great variety of pharmacological functions depending on the difference of the delicate chemical structure not seen in other chemical systems. These germanium compounds can be selected from commercially available products (e.g., powders, etc.) and used.

The above-described seawater concentrated solution is obtained by concentrating a seawater. The seawater as the source of life has various kinds of minerals with a good balance and is very superior in taking minerals with a good balance. However, since the seawater contains much salt, it is not preferable to take it in a large amount as it stands. Thus, in the present invention, the seawater is concentrated and the salt (NaCl) contained in the seawater during this step is eliminated, thereby reducing the salt content as small as possible. Then, a very slight amount of the water content (concentrated solution) which has finally remained is taken, whereby the minerals in this concentrated solution are used as active ingredients.

For example, the concentrated solution can be produced by the following process. A suitable amount of seawater is charged into a pot or other heating vessel and heated for concentration until the amount of the seawater has been reduced to about 30% of the initially charged amount. Subsequently, the resulting solution is cooled by spontaneous cooling or other means to deposit NaCl, which is then filtered out. The remaining water content is further heated for concentration until the amount of the seawater has been reduced to about 3 to 5% of the initially charged amount, followed by cooling. The thus cooled seawater is filtered to remove out the deposited NaCl. In this case, in order to achieve the filtration such that the water content does not remain in the deposited salt content, the filtration is carried out by filtration under reduction, if desired. The thus obtained filtrate is a seawater concentration solution containing minerals to be required for the physiological function as nutrients, such as calcium, iron, zinc, cobalt, and manganese, with a good balance.

Equipments which are used for the concentration of seawater are not specifically limited, but any equipments capable of performing the concentration can be used without specific limitations with respect to the heating manner, the processing temperature and time, the amount of seawater to be processed, and the like. The cooling step before the filtration is carried out for the purpose of increasing the amount of the deposited NaCl by lowering the water temperature. Furthermore, in order to improve the efficiency for obtaining the concentrated solution, the amount of seawater to be processed in one process is preferably 5 liters or more. The above-described concentration process of the seawater is merely shown as one example, and it is to be not construed that the present invention is limited to this processing process. Also, with respect to the concentration process, the heating under reduced pressure is preferable to the heating at atmospheric pressure.

As the above-described water, though usual drinking water such as tap water or underground water can be used, it is preferred to employ distilled water obtained by distilling such water, or pure water obtained by permeating such water through a hollow yarn membrane for achieving the sterilization.

The active water as one of the invention according to the present invention is obtained by mixing water with the above-described substance containing a divalent and trivalent iron salt component and the above-described organogermanium compound and/or seawater concentrated solution (the foregoing respective substances being soluble in water). The compounding ratios of the respective substances against water are not specifically limited but can be arbitrarily chosen depending on the purpose for use and the like. However, in order to expect the desired pharmacological and physiological functions for the medicinal use, the compounding ratios of the respective substances against water at the time of use (administration) are in the ranges of from about $2 \times 10^{-12}$ to $2 \times 10^{-4}$% by weight for the substance containing a divalent and trivalent iron salt component, from about 0.01 to 1% by weight for the organogermanium compound, and from about 0.01 to 3% by weight for the seawater concentrated solution, respectively. In this specification, the above-described units (% by weight) show the ratios to the whole amount of the active water containing water.

The active water of the present invention can be produced by mixing water with the above-described respective substances in the above-specified compounding ratios from the beginning. Also, it is free that the compounding ratios of the above-described respective substances to the whole amount are made high as, e.g., 100 times, and these substances are mixed in water to prepare a stock solution of the active water, which is then diluted in a predetermined magnification with water and used. In addition, as other means, the above-described substance containing a divalent and trivalent iron salt component can be mixed in the above-specified compounding ratio in water, followed by mixing therewith the organogermanium compound and/or seawater concentrated solution in the predetermined compounding ratio(s) at an arbitrary point, thereby producing the desired active water.

It has been clarified that the thus produced active water is an active water exhibiting pharmacological and physiological functions on account of the functions which each of the active substance containing a divalent and trivalent iron salt component and the organogermanium compound and/or the seawater concentrated solution possesses as well as a synergistic effect thereof. In the case where the active water is applied for the medicinal use, it is usually administered.

The active water as another invention according to the present invention comprises water having a substance containing a magnetic divalent and trivalent iron salt component and an organogermanium compound and/or a seawater concentrated solution contained therein.

Examples of the substance containing a magnetic divalent and trivalent iron salt component as an active ingredient of the active water according to another invention of the present invention include chemically processed magnetite. As a specific production process of this substance, one comprising the following steps is exemplified. That is, the substance is produced by a process comprising a step for dissolving magnetite in concentrated hydrochloric acid, a step for neutralizing this solution with a strong alkali such as sodium hydroxide, calcium hydroxide, potassium hydroxide, and lithium hydroxide, a step for concentrating the neutralized solution to obtain crystals, and a step for adding the crystals to a solution of magnetite semi-dissolved in concentrated hydrochloric acid. This production process is merely shown as one example, and it is to be not construed that the present invention is limited thereto.

The thus produced active substance has the following two remarkable characteristics. One is a characteristic made available by the electromagnetic processing. That is, utilizing the ferrimagnetism which the magnetite itself possesses, a magnetic field is applied to water, thereby activating the water. The magnetite has a considerably large saturation magnetization as high as 471 G (G: gauss) at ordinary temperatures as compared with other substances and is a ferromagnetic substance causing a spontaneous magnetization. For these reasons, if the magnetite acts on water, the water has the same characteristics as those of electromagnetically processed active water. In particular, since the above-described active substance is dissolved in water and co-present therein, it acts on the water more strongly and effectively as compared with the active water having a magnetic field applied thereto externally.

Another is a characteristic made available by the chemical processing. That is, the magnetite has such a property that it is dissolved in an acid to generate Fe2+ and Fe3+ ions. Utilizing the iron (Fe) ions of the magnetite represented by the chemical formulation, $Fe^{3+}(Fe^{2+}Fe^{3+})O_4$, the hydrogen bonding of water is broken, and the polarization is promoted, thereby activating the water. Since the water is in the form of a cluster, it is less in the polarization than single molecules and is stable. The iron ions of the magnetite act on this cluster and make the water molecule small to promote the polarization, thereby activating the water. Since the iron ions have various catalytic functions, they are also concerned with the growth of animals and plants.

In the present invention, though the active substance thus produced through these steps can be used alone, it can be supported on other compounds such as inorganic compounds, e.g., sodium chloride, magnesium chloride, and aluminum, fertilizers, e.g., ammonium sulfate and calcium phosphate, minerals, e.g., clays, aluminum oxide, and silicon oxide, and organic compounds, e.g., glucose and amino acids. Even in the latter case, the active substance can maintain its effects and effectively work.

The active water as another invention according to the present invention uses the above-described substance containing a magnetic divalent and trivalent iron salt component as an active ingredient. The active water according to this invention is obtained by mixing water with the substance containing a magnetic divalent and trivalent iron salt component and the above-described organogermanium compound and/or the above-described seawater concentrated solution (the foregoing respective substances being soluble in water). As same to in the previously described invention, the compounding ratios of the respective substance against water can be set up depending on the purpose for use and the like. However, in order to expect the pharmacological and physiological effects as desired in the present invention, the compounding ratios of the respective substances against water at the time of use (administration) are in the ranges of from about $2 \times 10^{-12}$ to $2 \times 10^{-4}\%$ by weight for the substance containing a magnetic divalent and trivalent iron salt component, from about 0.01 to 1% by weight for the organogermanium compound, and from about 0.01 to 3% by weight for the seawater concentration solution, respectively. As same to in the previously described invention, the active water of this invention can be produced by mixing water with the above-described respective substances in the above-specified compounding ratios from the beginning. Also, it is free that the compounding ratios of the above-described respective substances to the whole amount are made high, and these substances are mixed in water to prepare a stock solution of the active water, which is then diluted in a predetermined magnification with water and used. In addition, the active water of this invention can also be produced by the above-described other means.

It has been clarified that the thus produced active water is an active water exhibiting pharmacological and physiological functions owing to the functions which each of the active substance containing a magnetic divalent and trivalent iron salt component and the organogermanium compound and/or the seawater concentrated solution possesses as well as a synergistic effect thereof. In the case where the active water is applied for the medicinal use, it is usually administered.

The present invention will be described in more detail with reference to the following Examples. However, these Examples are merely shown as a part of the invention, and as a matter of course, it is to be not construed that the present invention is limited thereto.

EXAMPLE 1

(Production of Substance Containing Divalent and Trivalent Iron Salt Component)

Ferric chloride (1.0 mg) was added to 100 ml of an aqueous 0.5 N sodium hydroxide solution and stirred for dissolution, followed by allowing to stand for 24 hours. After removal of insoluble matters generated in the solution, the solution was neutralized with hydrochloric acid, concentrated under reduced pressure, and then dried for crystallization in a desiccator. The thus obtained crystals were added with 50 ml of an aqueous 80 wt % isopropyl alcohol solution for redissolution, and the solution was concentrated under reduced pressure. The solvent was removed off, and the residue was dried. The redissolution, the concentration, and the drying were repeated several times. There were thus obtained 0.25 mg of crystals A (active substance containing a divalent and trivalent iron salt component).

(Processing of Water)

A tap water was sterilized by permeation through a hollow yarn membrane to obtain pure water.

(Production of Active Water)

The above-described pure water was mixed with $2 \times 10^{-6}\%$ by weight and 0.05% by weight of the above-described organogermanium compound [formula (2)], and the mixture was stirred to obtain an active water.

EXAMPLE 2

(Production of Seawater Concentrated Solution)

A seawater (5 liters) was charged in a pot and heated. After the amount of the seawater had reduced to approximately a half amount, the filtration was carried out to remove dusts and foreign matters. The resulting seawater was again heated and concentrated under heating until the amount of the seawater had reduced to approximately 30% of the initially charged amount, followed by spontaneous cooling to deposit NaCl. After removal of the deposited NaCl by filtration, the remaining seawater was heated for concentration until the amount of the seawater had reduced to approximately 5% of the initially charged amount thereof, followed by cooling. The thus cooled seawater was filtered to remove off the deposited NaCl, thereby obtaining a seawater concentrated solution. The thus obtained concentrated solution contains many minerals with a good balance.

(Production of Active Water)

The pure water obtained in Example 1 was mixed with $2 \times 10^{-6}\%$ by weight of the crystals A obtained in Example 1 and 0.08% by weight of the above-described seawater concentrated solution, and the mixture was stirred to obtain an active water.

EXAMPLE 3

The pure water obtained in Example 1 was mixed with $2 \times 10^{-6}\%$ by weight of the crystals A obtained in Example 1, 0.05% by weight of the above-described organogermanium compound [formula (2)], and 0.05% by weight of the seawater concentrated solution obtained in Example 2, and the mixture was stirred to obtain an active water.

In accordance with Examples 1 to 3, the active waters possessing both of the superior pharmacological and physiological functions were obtained. In the cases where the organogermanium compound was replaced by each of other compounds [formulae (3) to (11)] than the foregoing compound represented by the formula (2), there were obtained substantially the same effects. Also, when the compounding ratios of the above-described crystals A, organogermanium compound [formula (2)], and seawater concentrated solution against the above-described pure water were changed within the above-specified ranges, active waters having respective characteristics were obtained.

Using the active water produced in Example 3, the following tests were carried out.

1. In Vivo Test to Human

Five human volunteers, the ages of whom were from 31 to 46 years, were an object of the test. These subjects were orally administered with the active water as produced in Example 3 at a dose of 50 cc per day for five months (long period of time). Before and two weeks after as well as three months and six months after the initiation of the administration of the active water, the bloods of the respective subjects in an amount of 20 cc were collected. Also, the other group was administered with the active water for two weeks (short of period of time).

2. Separation of Peripheral Blood Lymphocyte (PBL)

Mononuclears were separated from the fresh whole blood by means of the Philcoal-Hipack density gradient ultracentrifugation (Litton Bionetics, Rockville, Md.). The lymphocyte band on the interface was collected, and cells were precipitated by centrifugation, which were then washed twice with RPMI-1640. Subsequently, the cells were suspended in a complete medium (CM) composed of RPMI-1640, 10% (v/v) fetal bovine serum, 2 mM glutamine, 25 mM HEPES (pH 7.2), 50 units of penicillin, and 50 (m/ml of streptomycin (Grand Island Biologicals, Santa Clara, Calif.).

3. In Vitro Test

The mononuclears were prepared under the sterilized conditions as described and suspended in CM in a concentration of $2 \times 10^6$. The PBL was cultured together with the active water for 16 hours, and the NK activity was measured by the Cr release test.

4. NK Cell Activity

A process which is usually used for estimating the NK antitumor activity is one using the Cr release test. In this test, a constant number of target tumor cells labeled with chorimum-51 ($^{51}Cr$) are cultured together with various numbers of NK effector cells. The cellular lympholytic rate is calculated from the following equation:

$$\text{Cellular Lympholytic Rate (\%)} = \frac{(\text{Experimental Release}) - (\text{Spontaneous Release})}{(\text{Total Release}) - (\text{Spontaneous Release})} \times 100$$

In the above equation, the experimental release stands for the count in the supernatant obtained from a well containing the effector cells; the spontaneous release stands for the spontaneous release only in the medium; and the total release stands for the maximum count obtained by the lysis using a detergent. In this case, the NK effector cells are diluted four times and coated as a class of four groups thereof together with the tumor cells on a microtiter plate. In short, the NK effector cells were suspended in an amount of $5 \times 10^6$ per ml of the CM, one ml of which was then separated and poured into four wells, thereby fixing the ratios of the effector to the target cell at 100/1, 50/1, 25/1, and 12/1, respectively. Subsequently, the microtiter plate was subjected to centrifugation at 500 rpm for three minutes and cultured at 37° C. for four hours, followed by measuring the radiation does of the supernatant by means of a gamma counter. The isotope release rate was calculated according to the above-described equation.

The results of the foregoing test are as follows. (1) The active water significantly increased the NK activity two weeks after the initiation of the administration. The NK activity, the base value of which was 6.6, 11.9, 21.5, and 27, 5, respectively, increased to 21, 31.6, 40.7, and 54.1, respectively after the initiation of the administration, registering increases of 189–318%.

(2) Thereafter, as a result of continuing the administration, the NK activity further increased after two to five months.

(3) On the other hand, in the in vitro test, even if the peripheral blood lymphocytes are cultured together with the active water for 16 hours, the NK activity increases only by 15%.

It is evident from the foregoing results that the active water of the present invention is a strong biological response modifier (BRM) and is useful as a medicine to be used in the cancer immunotherapy.

EXAMPLE 4

(Production of Substance Containing Magnetic Divalent and Trivalent Iron Salt Component)

Magnetite (0.1 g) was added to 10 ml of concentrated hydrochloric acid and stirred for dissolution, followed by allowing to stand for 24 hours. To this solution was added 25 ml of an aqueous 2N sodium hydroxide solution, followed by allowing to stand for neutralization for 24 hours. The resulting solution was concentration under reduced pressure to deposit crystals, which were then dried in an air dryer. The crystals were added to 10 ml of ethyl alcohol for rinsing. The rinsing operation was repeated several times to purify the crystals, thereby obtaining an active substance (crystal). The yield was 0.88 g. Subsequently, 5 g of magnetite was added to 10 ml of concentrated hydrochloric acid and stirred for semi-dissolution, to which was then added 0.1 g of the active substance crystals as obtained in the foregoing steps. The mixture were well stirred and allowed to stand for 24 hours. A supernatant was separated from the insoluble magnetite by means of the decantation manner, thereby obtaining an active substance solution (a solution of the active substance containing a magnetic divalent and trivalent iron salt component).

(Production of Active Water)

The pure water as prepared in Example 1 was mixed with $2 \times 10^{-6}\%$ by weight of the above-described active substance solution and 0.05% by weight of the above-described organogermanium compound [formula (2)], and the mixture was stirred to obtain an active water.

EXAMPLE 5

The pure water as prepared in Example 1 was mixed with $2 \times 10^{-6}\%$ by weight of the active substance solution as obtained in Example 4 and 0.08% by weight of the seawater concentrated solution as prepared in Example 2, and the mixture was stirred to obtain an active water.

EXAMPLE 6

The pure water as prepared in Example 1 was mixed with $2 \times 10^{-6}\%$ by weight of the active substance solution as obtained in Example 4, 0.05% by weight of the above-described organogermanium compound [formula (2)], and 0.05% by weight of the seawater concentrated solution as prepared in Example 2, and the mixture was stirred to obtain an active water.

In accordance with Examples 4 to 6, the active waters possessing both of superior pharmacological and physiological functions were obtained. In the cases where the organogermanium compound was replaced by each of other compounds than the forgoing compound represented by the formula (2), there were obtained substantially the same effects. Also, when the compounding ratios of the above-described active substance solution, organogermanium compound [formula (2)], and seawater concentrated solution against the above-described pure water were changed within the above-specified ranges, active waters having respective characteristics were obtained.

In accordance with the present invention, a novel active water possessing both of pharmacological and physiological functions can be provided.

While the invention has been described in detail and with reference to specific embodiments thereof, it will be apparent to one skilled in the art that various changes and modifications can be made therein without departing from the spirit and scope thereof.

What is claimed is:

1. A composition comprising water, a salt containing a divalent iron ion and a trivalent iron ion, and an organogermanium compound.

2. A composition as claimed in claim 1, wherein the salt is represented by the following formula:

$$Fe^{+2}{}_m Fe^{+3}{}_n Cl_{2m+3n}$$

wherein m and n each represent a 1 or 2.

3. A composition as claimed in claim 1 wherein the salt is magnetic.

4. A composition as claimed in claim 1, wherein the amount of the salt ranges from about $2 \times 10^{-12}$ to about $2 \times 10^{-4}$% by weight based on the weight of the composition.

5. A composition as claimed in claim 1, wherein the amount of the organogermanium compound ranges from about 0.01 to about 1% by weight based on the weight of the composition.

* * * * *